United States Patent
Ladtkow et al.

(10) Patent No.: US 12,207,891 B2
(45) Date of Patent: Jan. 28, 2025

(54) SYSTEMS AND METHODS FOR ABLATION VISUALIZATION

(71) Applicant: Covidien LP, Mansfield, MA (US)

(72) Inventors: Casey M. Ladtkow, Erie, CO (US); Darion Peterson, Longmont, CO (US); Darren G. Girotto, Louisville, CO (US); Matthew Hemstreet, Denver, CO (US); Ryan S. Goss, Golden, CO (US); David W. Blue, Erie, CO (US); Ryan Sohlden, Lyons, CO (US)

(73) Assignee: Covidien LP, Mansfield, MA (US)

( * ) Notice: Subject to any disclaimer, the term of this patent is extended or adjusted under 35 U.S.C. 154(b) by 19 days.

(21) Appl. No.: 18/350,104

(22) Filed: Jul. 11, 2023

(65) Prior Publication Data
US 2023/0355322 A1 Nov. 9, 2023

Related U.S. Application Data

(63) Continuation of application No. 16/538,200, filed on Aug. 12, 2019, now Pat. No. 11,707,329.
(Continued)

(51) Int. Cl.
*A61B 34/20* (2016.01)
*A61B 5/055* (2006.01)
(Continued)

(52) U.S. Cl.
CPC .............. *A61B 34/20* (2016.02); *A61B 5/055* (2013.01); *A61B 6/032* (2013.01); *A61B 8/00* (2013.01);
(Continued)

(58) Field of Classification Search
CPC ......... A61B 34/20; A61B 34/10; A61B 34/25; A61B 90/37; A61B 5/055; A61B 6/032;
(Continued)

(56) References Cited

U.S. PATENT DOCUMENTS

| 5,515,160 A | 5/1996 | Schulz et al. |
| 5,528,699 A | 6/1996 | Obata et al. |

(Continued)

FOREIGN PATENT DOCUMENTS

| CN | 1788693 A | 6/2006 |
| CN | 101249001 A | 8/2008 |

(Continued)

OTHER PUBLICATIONS

Pfannenstiel 2018 MS thesis Electrical and Computer Engineering Department Kansas State University 48 pages (Year: 2018).*

(Continued)

*Primary Examiner* — Keith M Raymond
*Assistant Examiner* — Patrick M Mehl
(74) *Attorney, Agent, or Firm* — Carter, DeLuca & Farrell LLP

(57) ABSTRACT

The visualization method includes displaying three-dimensional image data of at least one anatomical feature of a patient, receiving user input of the target for placing an ablation needle in the at least one anatomical feature of the patient, determining the position and orientation of the ablation needle based on the user input, displaying an image of a virtual ablation needle in the three-dimensional image data of the at least one anatomical feature of the patient according to the determined position and orientation, receiving user input of parameters of operating the ablation needle, and displaying a three-dimensional representation of the result of operating the ablation needle according to the input parameters.

20 Claims, 18 Drawing Sheets
(15 of 18 Drawing Sheet(s) Filed in Color)

Related U.S. Application Data

(60) Provisional application No. 62/717,041, filed on Aug. 10, 2018.

(51) Int. Cl.
*A61B 6/03* (2006.01)
*A61B 8/00* (2006.01)
*A61B 18/00* (2006.01)
*A61B 18/18* (2006.01)
*A61B 34/00* (2016.01)
*A61B 34/10* (2016.01)
*A61B 90/00* (2016.01)

(52) U.S. Cl.
CPC .......... *A61B 18/1815* (2013.01); *A61B 34/10* (2016.02); *A61B 34/25* (2016.02); *A61B 90/37* (2016.02); *A61B 2018/00577* (2013.01); *A61B 2018/1869* (2013.01); *A61B 2034/104* (2016.02); *A61B 2034/105* (2016.02); *A61B 2034/107* (2016.02); *A61B 2034/254* (2016.02)

(58) Field of Classification Search
CPC . A61B 8/00; A61B 18/1815; A61B 2034/104; A61B 2034/105; A61B 2034/107; A61B 2034/254; A61B 2018/00577; A61B 2018/1869; A61B 2034/102; A61B 2034/101; A61B 2017/00132
See application file for complete search history.

(56) References Cited

U.S. PATENT DOCUMENTS

| | | | |
|---|---|---|---|
| 5,776,062 | A | 7/1998 | Nields |
| 5,788,636 | A | 8/1998 | Curley |
| 5,799,099 | A | 8/1998 | Wang et al. |
| 5,810,008 | A | 9/1998 | Dekel et al. |
| 5,817,022 | A | 10/1998 | Vesely |
| 5,825,908 | A | 10/1998 | Pieper et al. |
| 5,836,954 | A | 11/1998 | Heilbrun et al. |
| 5,842,473 | A | 12/1998 | Fenster et al. |
| 5,873,822 | A | 2/1999 | Ferre et al. |
| 5,891,030 | A | 4/1999 | Johnson et al. |
| 5,902,239 | A | 5/1999 | Buurman |
| 5,953,013 | A | 9/1999 | Shimizu |
| 5,954,648 | A | 9/1999 | Van Der Brug |
| 5,957,844 | A | 9/1999 | Dekel et al. |
| 5,967,980 | A | 10/1999 | Ferre et al. |
| 6,002,808 | A | 12/1999 | Freeman |
| 6,006,126 | A | 12/1999 | Cosman |
| 6,019,724 | A | 2/2000 | Gronningsaeter et al. |
| 6,052,477 | A | 4/2000 | Wang et al. |
| 6,081,577 | A | 6/2000 | Webber |
| 6,112,112 | A | 8/2000 | Gilhuijs et al. |
| 6,112,113 | A | 8/2000 | Van Der Brug et al. |
| 6,119,033 | A | 9/2000 | Spigelman et al. |
| 6,165,181 | A | 12/2000 | Heilbrun et al. |
| 6,167,296 | A | 12/2000 | Shahidi |
| 6,195,444 | B1 | 2/2001 | Simanovsky et al. |
| 6,203,497 | B1 | 3/2001 | Dekel et al. |
| 6,216,029 | B1 | 4/2001 | Paltieli |
| 6,226,542 | B1 | 5/2001 | Reisfeld |
| 6,259,943 | B1 | 7/2001 | Cosman et al. |
| 6,285,902 | B1 | 9/2001 | Kienzle, III et al. |
| 6,298,262 | B1 | 10/2001 | Franck et al. |
| 6,301,495 | B1 | 10/2001 | Gueziec et al. |
| 6,332,089 | B1 | 12/2001 | Acker et al. |
| 6,334,847 | B1 | 1/2002 | Fenster et al. |
| 6,338,716 | B1 | 1/2002 | Hossack et al. |
| 6,341,231 | B1 | 1/2002 | Ferre et al. |
| 6,343,936 | B1 | 2/2002 | Kaufman et al. |
| 6,379,302 | B1 | 4/2002 | Kessman et al. |
| 6,381,483 | B1 | 4/2002 | Hareyama et al. |
| 6,440,071 | B1 | 8/2002 | Slayton et al. |
| 6,442,417 | B1 | 8/2002 | Shahidi et al. |
| 6,466,815 | B1 | 10/2002 | Saito et al. |
| 6,470,207 | B1 | 10/2002 | Simon et al. |
| 6,477,275 | B1 | 11/2002 | Melikian et al. |
| 6,487,432 | B2 | 11/2002 | Slack |
| 6,505,065 | B1 | 1/2003 | Yanof et al. |
| 6,529,758 | B2 | 3/2003 | Shahidi |
| 6,539,247 | B2 | 3/2003 | Spetz |
| 6,540,679 | B2 | 4/2003 | Slayton et al. |
| 6,546,279 | B1 | 4/2003 | Bova et al. |
| 6,553,152 | B1 | 4/2003 | Miller et al. |
| 6,574,493 | B2 | 6/2003 | Rasche et al. |
| 6,612,980 | B2 | 9/2003 | Chen et al. |
| 6,669,635 | B2 | 12/2003 | Kessman et al. |
| 6,675,032 | B2 | 1/2004 | Chen et al. |
| 6,694,163 | B1 | 2/2004 | Vining |
| 6,711,429 | B1 | 3/2004 | Gilboa et al. |
| 6,724,930 | B1 | 4/2004 | Kosaka et al. |
| 6,731,966 | B1 | 5/2004 | Spigelman et al. |
| 6,733,458 | B1 | 5/2004 | Steins et al. |
| 6,751,361 | B1 | 6/2004 | Wagman |
| 6,754,374 | B1 | 6/2004 | Miller et al. |
| 6,772,002 | B2 | 8/2004 | Schmidt et al. |
| 6,812,933 | B1 | 11/2004 | Silver |
| 6,892,090 | B2 | 5/2005 | Verard et al. |
| 6,909,913 | B2 | 6/2005 | Vining |
| 6,920,347 | B2 | 7/2005 | Simon et al. |
| 6,925,319 | B2 | 8/2005 | McKinnon |
| 6,947,786 | B2 | 9/2005 | Simon et al. |
| 6,961,405 | B2 | 11/2005 | Scherch |
| 6,968,224 | B2 | 11/2005 | Kessman et al. |
| 6,969,352 | B2 | 11/2005 | Chiang et al. |
| 6,973,202 | B2 | 12/2005 | Mostafavi |
| 7,035,461 | B2 | 4/2006 | Luo et al. |
| 7,043,055 | B1 | 5/2006 | Silver |
| 7,043,064 | B2 | 5/2006 | Paik et al. |
| 7,050,845 | B2 | 5/2006 | Vilsmeier |
| 7,161,596 | B2 | 1/2007 | Hoile |
| 7,171,255 | B2 | 1/2007 | Holupka et al. |
| 7,204,254 | B2 | 4/2007 | Riaziat et al. |
| 7,215,990 | B2 | 5/2007 | Feussner et al. |
| 7,251,352 | B2 | 7/2007 | Sauer et al. |
| 7,259,762 | B2 | 8/2007 | Tanacs et al. |
| 7,302,288 | B1 | 11/2007 | Schellenberg |
| 7,333,644 | B2 | 2/2008 | Jerebko et al. |
| 7,343,026 | B2 | 3/2008 | Niwa et al. |
| 7,379,572 | B2 | 5/2008 | Yoshida et al. |
| 7,383,073 | B1 | 6/2008 | Abovitz et al. |
| 7,450,749 | B2 | 11/2008 | Rouet et al. |
| 7,452,357 | B2 | 11/2008 | Vlegele et al. |
| 7,457,443 | B2 | 11/2008 | Persky |
| 7,491,198 | B2 | 2/2009 | Kockro |
| 7,492,930 | B2 | 2/2009 | Leitner et al. |
| 7,496,173 | B2 | 2/2009 | Goldman et al. |
| 7,499,743 | B2 | 3/2009 | Vass et al. |
| 7,519,218 | B2 | 4/2009 | Takemoto et al. |
| 7,536,041 | B2 | 5/2009 | Pekar et al. |
| 7,567,697 | B2 | 7/2009 | Mostafavi |
| 7,570,987 | B2 | 8/2009 | Raabe et al. |
| 7,581,191 | B2 | 8/2009 | Rice et al. |
| 7,593,505 | B2 | 9/2009 | Saracen et al. |
| 7,623,250 | B2 | 11/2009 | Moctezuma de la Barrera et al. |
| 7,630,753 | B2 | 12/2009 | Simon et al. |
| 7,636,420 | B2 | 12/2009 | Spies et al. |
| 7,639,853 | B2 | 12/2009 | Olivera et al. |
| 7,643,663 | B2 | 1/2010 | Wiemker et al. |
| 7,672,705 | B2 | 3/2010 | Lachaine et al. |
| 7,689,019 | B2 | 3/2010 | Boese et al. |
| 7,780,084 | B2 | 8/2010 | Zhang et al. |
| 7,809,184 | B2 | 10/2010 | Neubauer et al. |
| 7,831,082 | B2 | 11/2010 | Holsing et al. |
| 7,844,087 | B2 | 11/2010 | Ray et al. |
| 7,853,305 | B2 | 12/2010 | Simon et al. |
| 7,856,130 | B2 | 12/2010 | Suri et al. |
| 7,860,331 | B2 | 12/2010 | Lal et al. |
| 7,860,548 | B2 | 12/2010 | McIntyre et al. |
| 7,873,400 | B2 | 1/2011 | Moctezuma De La Barrera et al. |
| 7,874,987 | B2 | 1/2011 | Altmann et al. |
| 7,876,937 | B2 | 1/2011 | Schildkraut et al. |
| 7,876,939 | B2 | 1/2011 | Yankelevitz et al. |

(56) References Cited

U.S. PATENT DOCUMENTS

| | | |
|---|---|---|
| 7,876,942 B2 | 1/2011 | Gilboa |
| 7,892,224 B2 | 2/2011 | Hartlep et al. |
| 7,894,663 B2 | 2/2011 | Berg et al. |
| 7,899,513 B2 | 3/2011 | Phillips et al. |
| 7,907,772 B2 | 3/2011 | Wang et al. |
| 7,912,258 B2 | 3/2011 | Warmath et al. |
| 7,916,918 B2 | 3/2011 | Suri et al. |
| 7,920,911 B2 | 4/2011 | Hoshino et al. |
| 7,953,265 B2 | 5/2011 | Sirohey et al. |
| 7,957,572 B2 | 6/2011 | Von Berg et al. |
| 7,970,174 B2 | 6/2011 | Goldbach |
| 8,000,442 B2 | 8/2011 | Lachaine et al. |
| 8,010,180 B2 | 8/2011 | Quaid et al. |
| 8,019,133 B2 | 9/2011 | Knoplioch et al. |
| 8,023,712 B2 | 9/2011 | Ikuma et al. |
| 8,023,734 B2 | 9/2011 | Jolly et al. |
| 8,036,435 B2 | 10/2011 | Partain et al. |
| 8,045,778 B2 | 10/2011 | Blaffert et al. |
| 8,046,052 B2 | 10/2011 | Verard et al. |
| 8,750,568 B2 | 6/2014 | Frank et al. |
| 9,439,622 B2 | 9/2016 | Case et al. |
| 9,439,623 B2 | 9/2016 | Frank et al. |
| 9,439,627 B2 | 9/2016 | Case et al. |
| 9,498,182 B2 | 11/2016 | Case et al. |
| 11,707,329 B2 | 7/2023 | Ladtkow et al. |
| 2001/0027272 A1 | 10/2001 | Saito et al. |
| 2003/0135115 A1 | 7/2003 | Burdette et al. |
| 2003/0151665 A1 | 8/2003 | Uchiyama |
| 2003/0163142 A1 | 8/2003 | Paltieli et al. |
| 2004/0015070 A1 | 1/2004 | Liang et al. |
| 2004/0034297 A1 | 2/2004 | Darrow et al. |
| 2004/0138555 A1 | 7/2004 | Krag et al. |
| 2005/0215854 A1 | 9/2005 | Ozaki et al. |
| 2006/0229594 A1 | 10/2006 | Francischelli et al. |
| 2007/0238961 A1 | 10/2007 | Vilsmeier et al. |
| 2008/0063136 A1 | 3/2008 | Ohyu et al. |
| 2008/0081982 A1 | 4/2008 | Simon et al. |
| 2008/0097186 A1 | 4/2008 | Biglieri et al. |
| 2008/0119712 A1 | 5/2008 | Lloyd |
| 2008/0123921 A1 | 5/2008 | Gielen et al. |
| 2008/0123927 A1 | 5/2008 | Miga et al. |
| 2008/0167547 A1 | 7/2008 | Bova et al. |
| 2008/0200794 A1 | 8/2008 | Teichman et al. |
| 2008/0200926 A1 | 8/2008 | Verard et al. |
| 2008/0200927 A1 | 8/2008 | Hartmann et al. |
| 2008/0208041 A1 | 8/2008 | Gilboa |
| 2008/0214922 A1 | 9/2008 | Hartmann et al. |
| 2008/0221650 A1 | 9/2008 | Turner et al. |
| 2008/0232656 A1 | 9/2008 | Voegele |
| 2008/0242978 A1 | 10/2008 | Simon et al. |
| 2008/0262345 A1 | 10/2008 | Fichtinger et al. |
| 2008/0285854 A1 | 11/2008 | Kotake et al. |
| 2009/0028436 A1 | 1/2009 | Yoshino et al. |
| 2009/0124896 A1 | 5/2009 | Haras |
| 2009/0198126 A1 | 8/2009 | Klingenbeck-Regn |
| 2009/0221908 A1 | 9/2009 | Glossop |
| 2009/0292201 A1 | 11/2009 | Kruecker |
| 2009/0312629 A1 | 12/2009 | Razzaque et al. |
| 2010/0063392 A1 | 3/2010 | Nishina et al. |
| 2010/0063496 A1 | 3/2010 | Trovato et al. |
| 2010/0076305 A1 | 3/2010 | Maier-Hein et al. |
| 2010/0121189 A1 | 5/2010 | Ma et al. |
| 2010/0121190 A1 | 5/2010 | Pagoulatos et al. |
| 2010/0168763 A1 | 7/2010 | Zhao et al. |
| 2010/0179529 A1 | 7/2010 | Podhajsky et al. |
| 2010/0208963 A1 | 8/2010 | Kruecker et al. |
| 2010/0217117 A1 | 8/2010 | Glossop et al. |
| 2010/0249771 A1 | 9/2010 | Pearson et al. |
| 2010/0250209 A1 | 9/2010 | Pearson et al. |
| 2010/0259474 A1 | 10/2010 | Hildreth |
| 2010/0268223 A1 | 10/2010 | Coe et al. |
| 2010/0274124 A1 | 10/2010 | Jascob et al. |
| 2010/0277655 A1 | 11/2010 | Sun |
| 2010/0295931 A1 | 11/2010 | Schmidt |
| 2010/0298705 A1 | 11/2010 | Pelissier et al. |
| 2010/0312103 A1 | 12/2010 | Gorek et al. |
| 2010/0322489 A1 | 12/2010 | Tizhoosh et al. |
| 2011/0015628 A1 | 1/2011 | Dalal et al. |
| 2011/0118596 A1 | 5/2011 | Vining et al. |
| 2011/0129154 A1 | 6/2011 | Shimodaira |
| 2011/0137156 A1 | 6/2011 | Razzaque et al. |
| 2011/0137168 A1 | 6/2011 | Lee et al. |
| 2011/0160569 A1 | 6/2011 | Cohen et al. |
| 2011/0251483 A1 | 10/2011 | Razzaque et al. |
| 2012/0050258 A1 | 3/2012 | Kay et al. |
| 2012/0136242 A1 | 5/2012 | Qi et al. |
| 2012/0277585 A1 | 11/2012 | Koenig et al. |
| 2013/0142410 A1 | 6/2013 | Dwivedi et al. |
| 2013/0316318 A1 | 11/2013 | Frank et al. |
| 2014/0206988 A1 | 7/2014 | Ramachandran et al. |
| 2015/0282786 A1 | 10/2015 | Anand et al. |
| 2016/0038247 A1 | 2/2016 | Bharadwaj et al. |
| 2016/0038248 A1 | 2/2016 | Bharadwaj et al. |
| 2018/0008341 A1 | 1/2018 | Brannan |
| 2018/0028267 A1 | 2/2018 | Onik et al. |

FOREIGN PATENT DOCUMENTS

| | | |
|---|---|---|
| CN | 201422889 Y | 3/2010 |
| DE | 10 2008 013611 A1 | 9/2009 |
| EP | 1571581 A1 | 9/2005 |
| EP | 1649822 A1 | 4/2006 |
| WO | 9515729 A1 | 6/1995 |
| WO | 9703609 A1 | 2/1997 |
| WO | 0139124 A2 | 5/2001 |
| WO | 2006089426 A1 | 8/2006 |
| WO | 12007113815 A2 | 10/2007 |
| WO | 2008017051 A2 | 2/2008 |
| WO | 2008058520 A2 | 5/2008 |
| WO | 2012025842 A2 | 3/2012 |
| WO | 2012066446 A1 | 5/2012 |

OTHER PUBLICATIONS

Mathias Markert "Development of an assistance system for open liver surgery usable in clinical interventions" submitted Jan. 31, 2011, <http://mediatum.ub.tum.de?id=1007285>.

International Search Report and Written Opinion of the International Searching Authority issued in corresponding Appl. No. PCT/US2019/046152 mailed Oct. 31, 2019 (16 pages).

Kosaka A. et al. "Augmented Reality System for Surgical Navigation Using Robust Target Vision", Proceedings 2000 IEEE Conference on Computer Vision and Pattern Recognition. CVPR 2000. Hilton Head Island, SC, Jun. 13-15, 2000, pp. 187-194.

\* cited by examiner

SYSTEMS AND METHODS FOR ABLATION VISUALIZATION

CROSS-REFERENCE TO RELATED APPLICATIONS

This application is a continuation of U.S. patent application Ser. No. 16/538,200, filed on Aug. 12, 2019, now U.S. Pat. No. 11,707,329, which claims the benefit of the filing date of provisional U.S. Patent Application No. 62/717,041, filed on Aug. 10, 2018.

INTRODUCTION

This disclosure relates to visualizing a treatment procedure and, more particularly, to systems and methods for visualizing the anatomy of a patient based on parameters of operating an ablation probe.

BACKGROUND

Computed tomography (CT) images are commonly used to identify objects, such as physiological structures, in a patient's body. In particular, CT images can be used by physicians to identify malignant tissue or problematic structures in a patient's body and to determine their location within the body. Once the location is determined, a treatment plan can be created to address the problem, such as planning a pathway into the patient's body to remove malignant tissue or planning procedures for accessing and altering the problematic structures. Ablation of tumors is an example of a more targeted approach to tumor treatment. In comparison to traditional body-wide types of cancer treatment, such as chemotherapy, ablation technologies are more targeted and limited, but are just as effective. Thus, such approaches are beneficial in providing targeted treatment that limits unnecessary injury to non-problematic tissue or structures in the patient's body, but they require the assistance of more complex technical tools. Accordingly, there continues to be interest in developing further technical tools to assist with targeted treatment of tissue or structural problems in a patient's body.

SUMMARY

This disclosure relates generally to visualization systems and methods for visualizing potential ablation size in three dimensions overlaid on or incorporated into images of patient anatomy. In one aspect, this disclosure features a method of performing an ablation procedure. The method includes displaying three-dimensional image data of at least one anatomical feature of a patient, receiving user input of the target for placing an ablation needle in the at least one anatomical feature of the patient, determining the position and orientation of the ablation needle based on the user input, displaying an image of a virtual ablation needle in the three-dimensional image data of the at least one anatomical feature of the patient according to the determined position and orientation, receiving user input of parameters of operating the ablation needle, and displaying a three-dimensional representation of the result of operating the ablation needle according to the input parameters.

In aspects, the method includes receiving further user input of movement of an ablation needle in the at least one anatomical feature of the patient, determining the new position and orientation of the ablation needle based on the further user input, and displaying the virtual ablation needle in the three-dimensional image according to the determined further position and orientation.

In aspects, the method includes receiving user input of other different parameters of operating the ablation needle, and displaying a three-dimensional representation of the result of operating the ablation needle according to the other different parameters.

In aspects, the method includes displaying a default ablation zone relative to the target, receiving user input adjusting the size of the ablation zone, calculating ablation time based on the adjusted size of the ablation zone, and displaying the calculated ablation time.

In aspects, the method includes calculating a tip distance based on the adjusted size of the ablation zone, and displaying the calculated tip distance.

In aspects, the parameters of operating the ablation needle include power level and ablation needle type.

In aspects, the three-dimensional representation of the result of operating the ablation needle is a three-dimensional representation of at least one of a temperature profile, an ablation zone, potential histological zones, a plurality of temperatures, confidence intervals, a heated zone, or probability of cell death with respect to the position of the ablation needle.

In aspects, displaying the three-dimensional image includes displaying a multi-plane view including at least two of a coronal view, a sagittal view, an axial view, or a three-dimensional view of that ablation needle and the ablation zone.

In aspects, the method includes displaying user-selectable icons for selecting a skin view, a muscle view, or a bone view of at least a portion of the patient.

In aspects, the method includes displaying a single-slice view including a coronal view, a sagittal view, or an axial view, and displaying user-selectable icons for selecting between the coronal view, the sagittal view, or the axial view.

In aspects, the method includes simultaneously displaying a different one of the coronal view, the sagittal view, or the axial view, displaying a user-movable cross-section line on the different one of the coronal view, the sagittal view, or the axial view, and displaying a slice corresponding to the position of the cross-section line.

In aspects, the three-dimensional image data is at least one of computed tomography image data, magnetic resonance image data, or ultrasound image data.

In aspects, the method includes displaying a snapshot button, receiving user selection of the snapshot button, and recording an image including an image of the anatomy, a target, an ablation zone, and text indicating the power level and the ablation time.

In another aspect, this disclosure features an ablation visualization system, which includes a display, a processor, and a memory having stored thereon instructions which are executed by the processor. When the instructions are executed by the processor, the processor displays, on the display, three-dimensional image data of at least one anatomical feature of a patient on the display, prompts a user for input of a target for placing an ablation needle in the at least one anatomical feature of the patient, receives user input of the target for placing the ablation needle in the at least one anatomical feature of the patient, determines a position and orientation of the ablation needle based on the user input, displays, on the display, an image of a virtual ablation needle in the three-dimensional image data of the at least one anatomical feature of the patient according to the determined position and orientation, prompts the user for input of parameters of operating the ablation needle, receives user input of parameters of operating the ablation needle, and displays, on the display, a three-dimensional representation of a result of operating the ablation needle according to the input parameters.

In aspects, the instructions, when executed by the processor, further cause the processor to prompt for further user input of movement of an ablation needle in the at least one anatomical feature of the patient, receive further user input of movement of an ablation needle in the at least one anatomical feature of the patient, determine a new position and orientation of the ablation needle based on the further user input, and display the virtual ablation needle in the three-dimensional image according to the new position and orientation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various aspects and features of this disclosure are described below with references to the drawings, of which.

DETAILED DESCRIPTION

Figure 1:
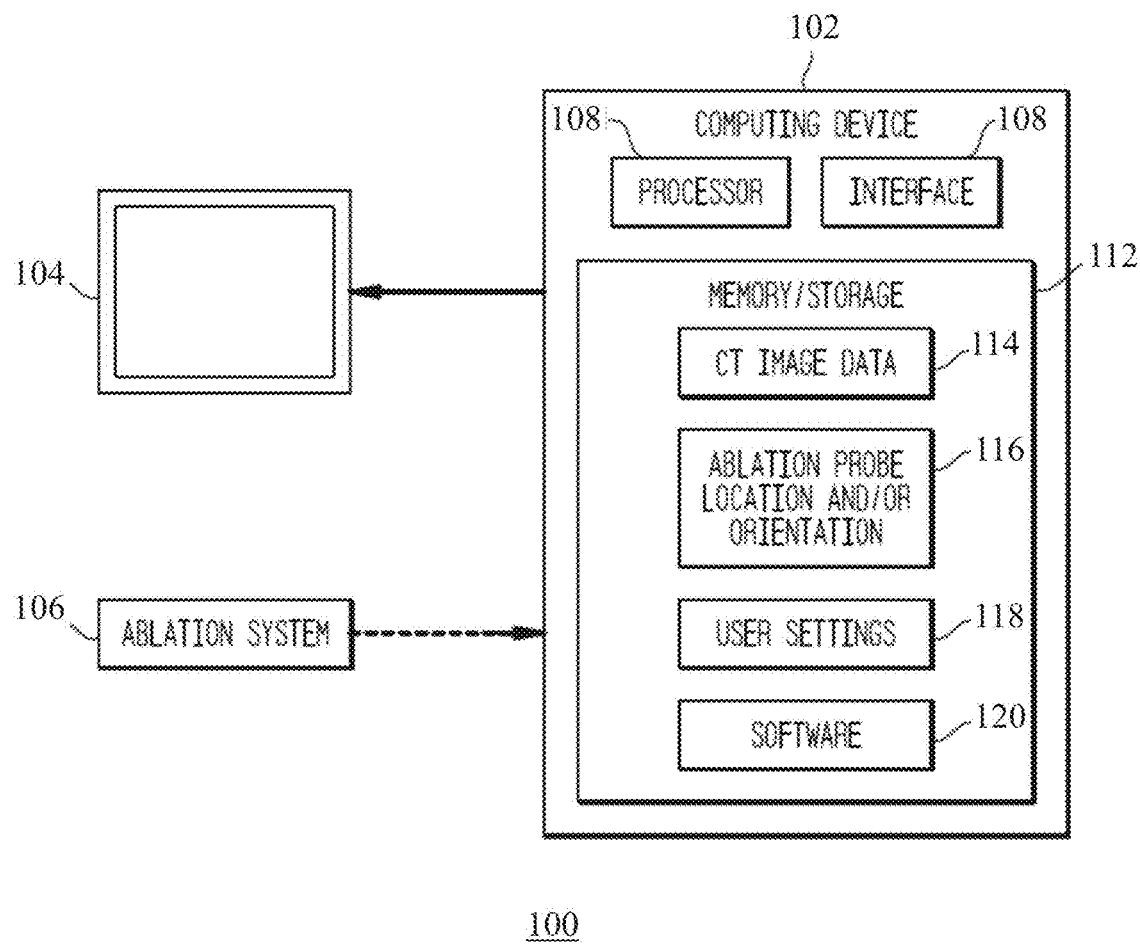
FIG. 1 is a block diagram of an exemplary system for ablation visualization in accordance with aspects of this disclosure.

Embodiments of this disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the phrase "in embodiments" and variations on this phrase generally is understood to mean that the particular feature, structure, system, or method being described includes at least one iteration of the disclosed technology. Such phrase should not be read or interpreted to mean that the particular feature, structure, system, or method described is either the best or the only way in which the embodiment can be implemented. Rather, such a phrase should be read to mean an example of a way in which the described technology could be implemented, but need not be the only way to do so.

In order for physicians or clinicians to perform ablations and achieve good clinical outcomes, they need to achieve an ablative margin. Achieving an ablative margin requires understanding where the ablation device will create lethal heating. This is a three-dimensional problem and involves understanding the gradient of temperature created by a particular ablation device at a particular power and time. Some ablation devices provide tables of power, time, and ablation size. These tables are often derived from Ex Vivo models and provide the mean value for each dimension, but leave out statistical information such as sample size and standard deviation. The information in these tables is used during a procedure to select the correct power and time via a manual process where, for example, the physician or clinician visualizes the ablation device on a CT scan and uses a linear measurement tool to estimate the location of the planned ablation on a screen. This process, however, does not take into account the three-dimensional nature of ablation planning, nor does it take into account the inherent variability of the ablation device being used.

This disclosure provides multiple visualization techniques that allow for visualizing potential ablation size in three dimensions overlaid on or incorporated into images of patient anatomy. By overlaying or incorporating visualizations that include different measures of variability in device performance on images of actual patient anatomy, the visualization techniques or methods of this disclosure maximize the information communicated in a single visualization.

The visualization techniques provide an understanding of ablation potential in the context of the actual patient anatomy. The overlay or incorporation of ablation information on CT, MR, or US image data brings context to ablation performance data. The visualization techniques allow for ablation performance to be visualized with respect to actual and/or planned needle position and patient anatomy at the same time in a single view, thereby recreating the entire context of the ablation. This can be done before the needle is placed as a planning step or after the actual needle is in place to aid in final adjustments of needle position or power and time.

The methods of this disclosure also allow for the physician or clinician to visualize temperatures, histological damage, potential histological zones, confidence intervals or probability of cell death, and ablation potential with reference to the needle and the patient anatomy.

Referring now to FIG. 1, there is shown a block diagram of a system 100, which includes a computing device 102 such as, for example, a laptop, desktop, workstation, tablet, or other similar device, a display 104, and an ablation system 106. The computing device 102 includes one or more processors 108, interface devices 110 (such as communications interface and user interface), memory and storage 112, and/or other components generally present in a computing device. The display 104 may be touch sensitive, which enables the display to serve as both an input and output device. In various embodiments, a keyboard (not shown), mouse (not shown), or other data input devices may be employed.

Memory/storage 112 may be any non-transitory, volatile or non-volatile, removable or non-removable media for storage of information such as computer-readable instructions, data structures, program modules or other data. In various embodiments, the memory 112 may include one or more solid-state storage devices such as flash memory chips or mass storage devices. In various embodiments, the memory/storage 112 can be RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 102.

Computing device 102 may also include an interface device 110 connected to a network or the Internet via a wired or wireless connection for the transmission and reception of data. For example, computing device 102 may receive computed tomographic (CT) image data 214 of a patient from a server, for example, a hospital server, Internet server, or other similar servers, for use during surgical ablation planning. Patient CT image data 114 may also be provided to computing device 202 via a removable memory.

In the illustrated embodiment, the memory/storage 112 includes CT image data 114 for one or more patients, information regarding the location and orientation of an ablation probe 116, various user settings 118 (which are described below), and various software that perform the operations described herein 120.

In various embodiments, the system 100 includes an ablation system 106 that includes a generator (not shown) and an ablation probe that includes an ablation antenna. The ablation system 106 will be described in more detail later herein.

Figure 2:
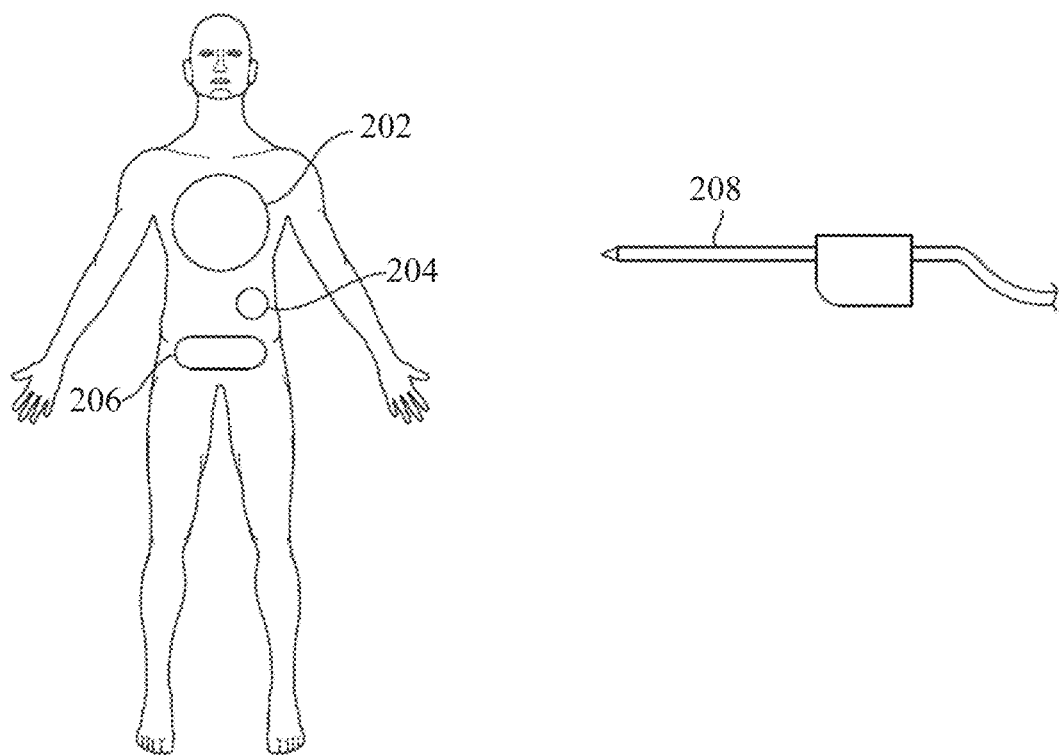
FIG. 2 is a diagram of exemplary regions of a patient to which the disclosed systems and methods may be applied.

In accordance with an aspect of this disclosure, the software 120 of FIG. 1 includes a treatment planning module which guides a clinician in identifying a target for ablation treatment, a target size, a treatment zone, and an access route to the target. As used herein, the term "clinician" refers to any medical professional (e.g., doctor, surgeon, nurse, physician assistant, technician, or the like) for planning, performing, monitoring and/or supervising a medical procedure involving the use of the embodiments described herein. The treatment planning module can generate a user interface screen for presenting information and receiving clinician input. The clinician can select a patient data set corresponding to a patient via the user interface. With reference also to FIG. 2, a patient data set can be selected based on, for example, a region where the ablation target is located, such as a lung region 202, a liver region 204, a kidney region 206, or another region of the patient. The patient data set includes CT image data for the selected region 202-206, which will be described below in connection with FIGS. 3-7.

As persons skilled in the art will understand, CT image data are x-ray scans of "slices" of a patient's anatomy. Although each slice views the anatomy from a particular angle, image data across multiple "slices" can be used to generate views of the anatomy from other angles. Based on the position and orientation of an ablation probe, an image of the anatomy can be generated for a probe-axial view, a probe-sagittal view, and a probe-coronal view. FIGS. 3-6 illustrate examples of these different views for a lung region 202. The lung region 202 is merely exemplary, and as mentioned above, other regions of the body can be viewed as well.

Figure 3A:
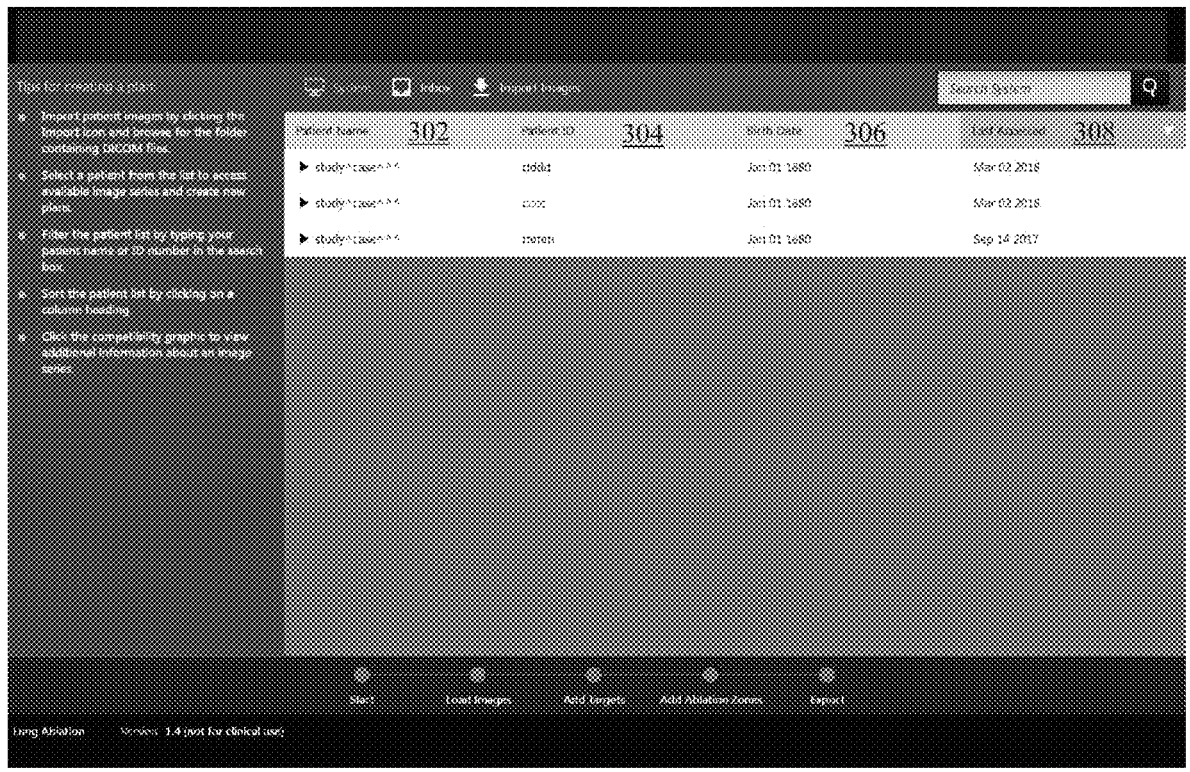
FIGS. 3A and 3B are exemplary display interfaces for viewing and selecting patient image data that is used to view or create a surgical plan in accordance with aspects of this disclosure.
Figure 3B:
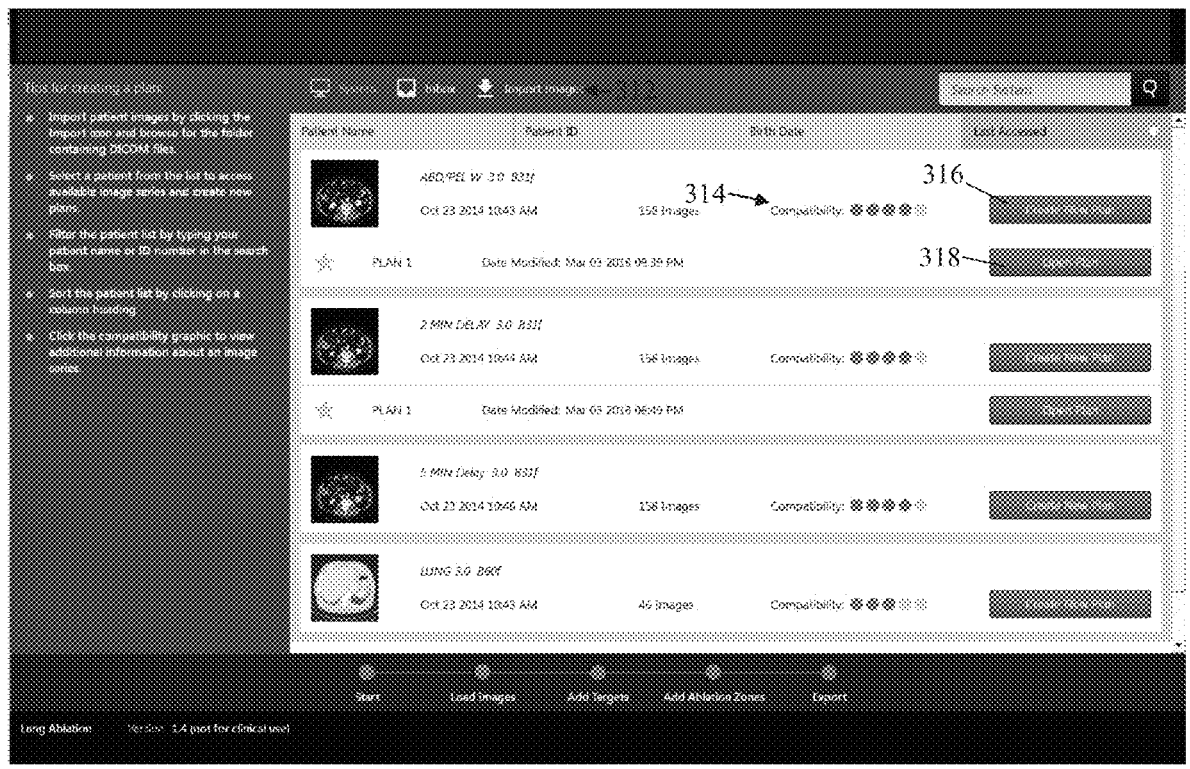

FIGS. 3A and 3B are exemplary display interfaces for viewing and selecting patient image data that is used to view or create a surgical plan in accordance with aspects of this disclosure. To import image data into the system, the user, such as a clinician, selects the "Import Images" icon 312 and selects an image data file in a file system browser window (not shown), which may be displayed in response to a user selecting the "Import Images" icon 312.

After importing image data into the system, information identifying the image data is arranged in the display interface of FIG. 3A. The information for identifying the image data includes patient name 302, patient identification (ID) 304, birth date 306, and date on which the image data for a particular patient was accessed 308. The clinician can use this information to navigate to the image data of a given patient for whom a surgical plan will be created. The display interface includes "Tips for creating a plan" to guide the clinician through the step of creating a surgical plan. This allows the clinician to navigate through the various display interfaces of the system without having to open a separate window, such as a help window. Alternatively, the clinician may quickly locate the image data of a patient by entering a patient name, identification number, or other identifying information in the search field and selecting the search execution button.

To create a new plan or open an existing plan for a patient, the clinician selects the patient name in the display interface of FIG. 3A, which causes the display interface of FIG. 3B to be displayed. The display interface of FIG. 3B shows one or more series of images corresponding to a selected patient. For each series of images, there is a "Create New Plan" icon, which, when selected by a clinician starts the process of creating a surgical plan. If one or more plans have been created for a particular series of images, an "Open Plan" icon is provided, which, when selected by a clinician, allows the clinician to review and/or revise that particular plan. Each series of images also shows compatibility level 314, which may indicate the compatibility of the series of images with the system. For example, a lower compatibility level may indicate that the series of images make it difficult to take advantage of the planning features of the system.

Figure 4:
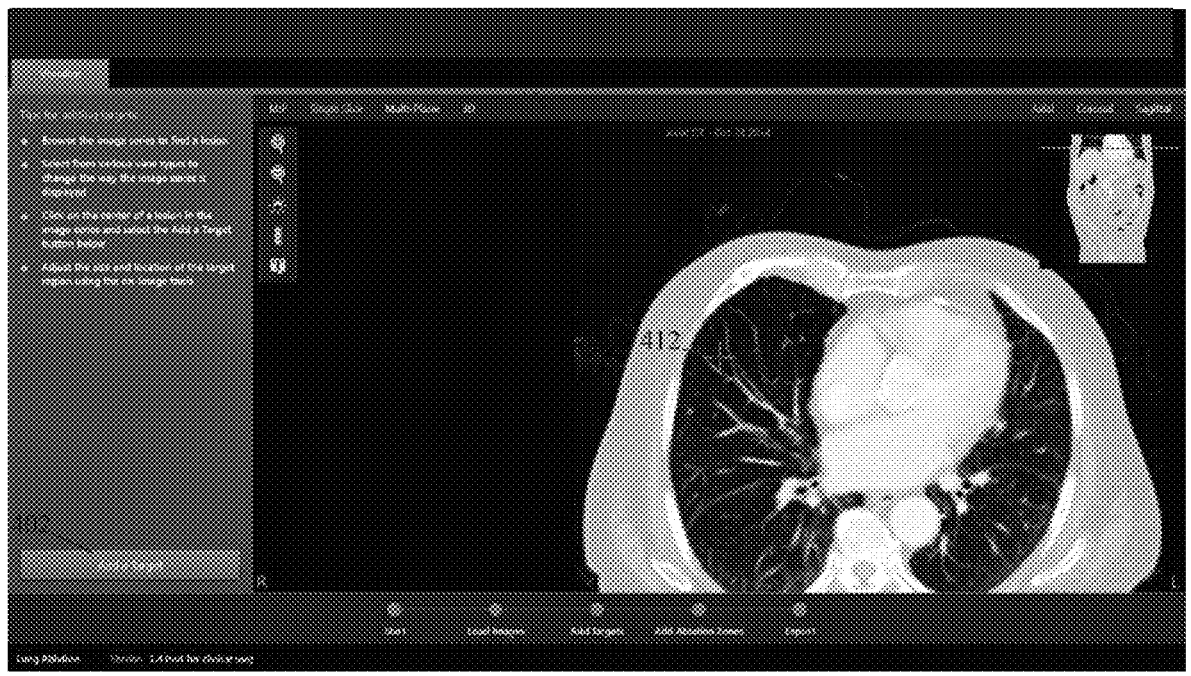
FIG. 4 is an exemplary display interface for adding targets to patient image data in accordance with aspects of this disclosure.
Figure 5A:
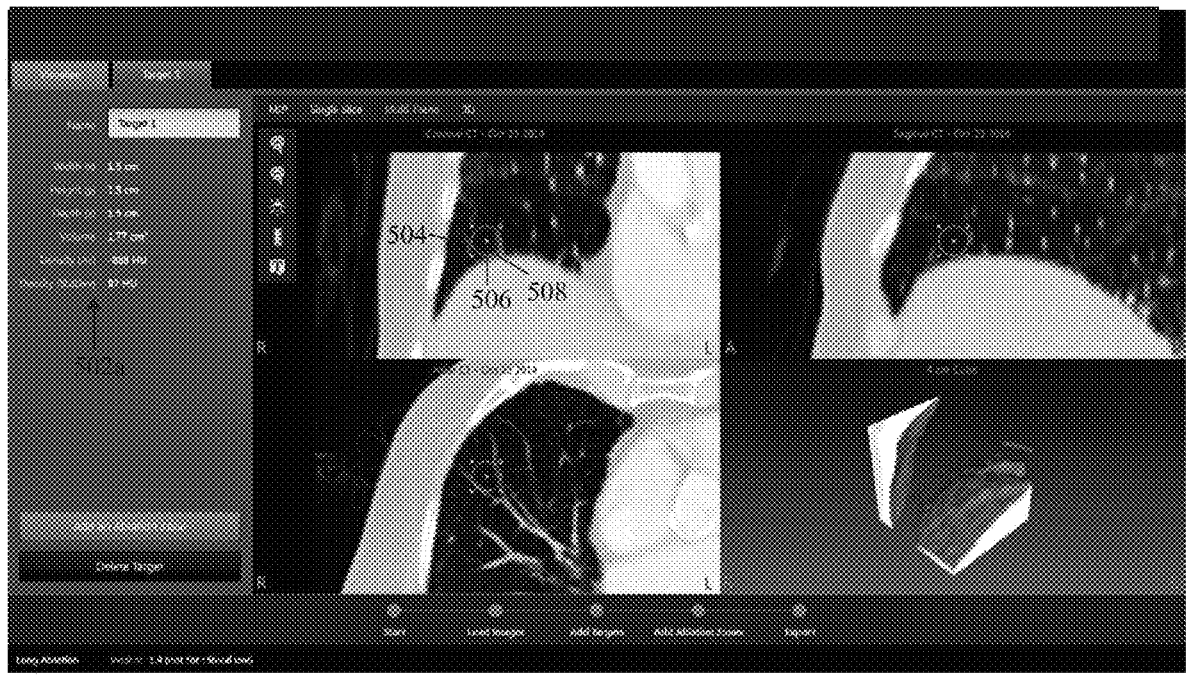
FIGS. 5A and 5B are exemplary display interfaces for viewing and modifying an added target in accordance with aspects of this disclosure.

When the clinician selects the "Create New Plan" icon or button shown in FIG. 3B, the "Visualize" interface is displayed, as shown in FIG. 4. The "Visualize" interface allows the clinician to browse different views of the series of images to locate a lesion or other target surgical site and to add a target. The "Visualize" interface of FIG. 4 includes selectable icons 404 to select from among multiple views. The multiple views may include a Maximum Intensity Projection (MIP) view, a single slice view (which is shown as selected in FIG. 4), a multi-plane view, and a three-dimensional (3D) view. In the single slice view, the "Visualize" interface of FIG. 4 also includes selectable icons 406 for selecting between an axial view (which is shown as selected in FIG. 4), a coronal view, and a sagittal view. In the single slice view, the clinician can browse through a series of images to locate a lesion. When the clinician locates a lesion or target surgical site, the clinician may click a mouse button at the center of a legion to place a crosshair icon 412 at the center of the legion. The clinician then adds that target location to the series of images by selecting the "Add a target" button 402, which causes the system to open a target window and corresponding tab, as illustrated in FIG. 5A.

Upon opening the target window, a multiplane view may initially be shown. The multiplane view includes a coronal image, a sagittal image, an axial image, and a 4 cm cube centered on the target location. In the target window, a target region centered at the target location may initially be identified by a circle 504 of a predetermined size, a selectably movable point 506 at the target location, and a plurality of selectably movable points 508 for changing the size and shape of the target region in each of the coronal view, the sagittal view, and the axial view. Textual information regarding the initial target region 502a may also be displayed in the target window. The textual information may include the width (x), the height (y), the depth (z), the volume, and the density of the target region. In this example, the width is 1.5 cm, the height is 1.5 cm, the depth is 1.5 cm, the volume is 1.77 cm$^2$, the density (average) is −889 HU, and the density (standard deviation) is 87 HU.

Figure 5B:

The clinician may change the size and shape of the target region 504 by selecting and moving one or more of the plurality of point 508. For example, may change the size and shape of the target region 504 as illustrated in FIG. 5B, which results in new textual information 502b. In this example, the new width is 1.0 cm, the new depth is 1.1 cm, the new volume is 0.83 cm$^2$, the density (average) is −924 HU, and the density (standard deviation) is 38 HU. When the clinician finishes defining the size and shape of the target region 504, the clinician may select the "Add an Ablation Zone" button 402.

Figure 6A:
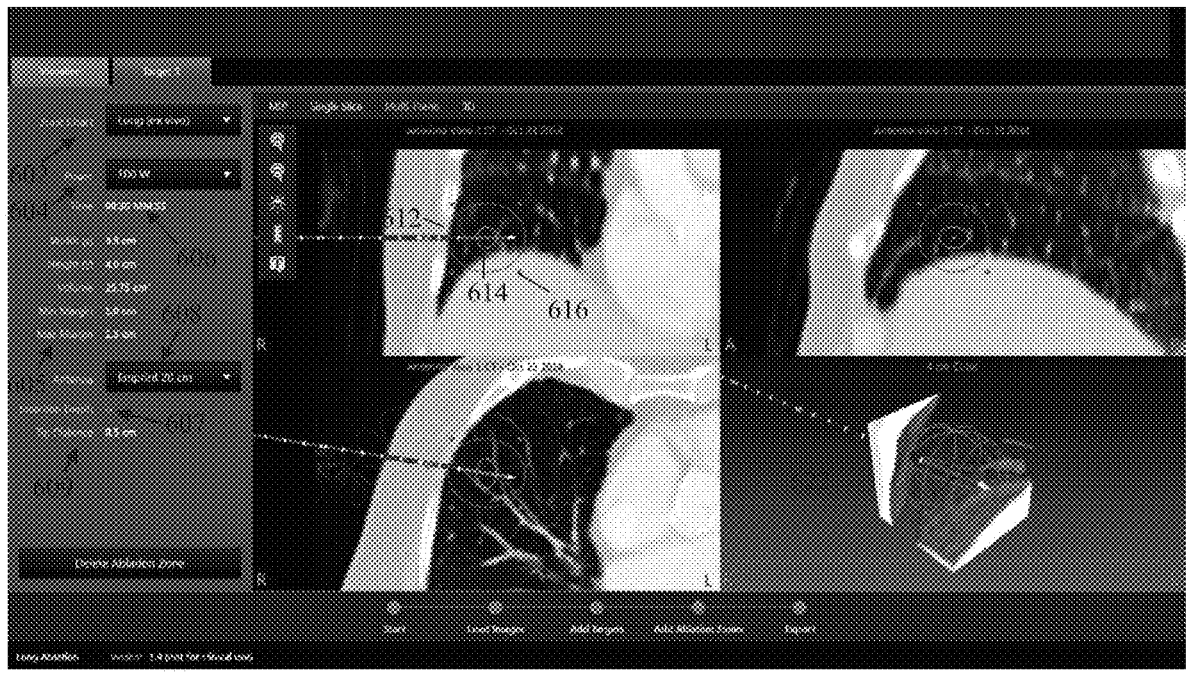
FIGS. 6A and 6B are exemplary display interfaces for viewing and modifying various ablation parameters in accordance with aspects of this disclosure.

When the clinician selects the "Add an Ablation Zone" button 402, the display interface of FIG. 6A is displayed. The display interface of FIG. 6A shows an ablation antenna or probe 611, an initial ablation zone 612, a selectably movable point 614 at the target location, and a plurality of selectably movable points 616 for changing the size and shape of the ablation zone are displayed in each of the axial view, the coronal view, and the sagittal view. Also, a three-dimensional wireframe representation of the ablation zone is displayed in the 4 cm Cube view 622, and textual information and user-selectable operation settings regarding the ablation antenna and the ablation zone are displayed in the target window.

The user-selectable operation settings include a zone chart setting 602, a power setting 604, and an antenna type setting 608. The textual information includes an ablation time 606, ablation zone information 605, an insertion depth 607, and a tip distance 609. The ablation zone information 605 includes the width (x), the height (y), the volume, the min margin, and the max margin of the ablation zone. In the example of FIG. 6A, the initial time 606 is 8 minutes and 30 seconds, the initial width is 3.5 cm, the initial height is 4.0 cm, the initial volume is 25.75 cm$^3$, the initial min margin is 1.0 cm, the initial max margin is 1.5 cm, the initial insertion depth 607 is "--", and the initial tip distance 609 is 0.5 cm.

The zone chart setting 602, the power setting 604, and the antenna type setting 608 are each configured to receive user input though a pull-down menu. The pull-down menu for the zone chart setting 602 may include a "Lung (ex vivo)" menu item and a "Lung (in vivo)" menu item that a user can select between. The pull-down menu for the power level setting 604 may include a "45 W" menu item, a "75 W" menu item, and a "100 W" menu item. In some embodiments, the pull-down menu for the power level setting 604 may include other menu items corresponding to other power levels, depending on the type of microwave generator that is being used or other factors. In other embodiments, the power level setting 604 may be set via a text field in which the user can enter a power level value. The pull-down menu for the antenna type setting 608 may include a "15 cm" menu item, a "20 cm" menu item, and a "30 cm" menu item.

As shown in FIG. 6A, the zone chart setting 602 is initially set to "Lung (ex vivo)", the power setting is initially set to 100 W, and the antenna type setting 608 is initially set to "Emprint 20 cm". The textual information including the time information 606 is configured to change based on the user selecting one or more of the user-selectable menu items, the user changing the size or position of the ablation zone, or the user changing the position of the antenna. This allows the user to visualize an ablation procedure if one or more parameters of the ablation procedure are changed. In this way, the user can determine the optimal parameters for the ablation procedure to be performed.

Figure 6B:
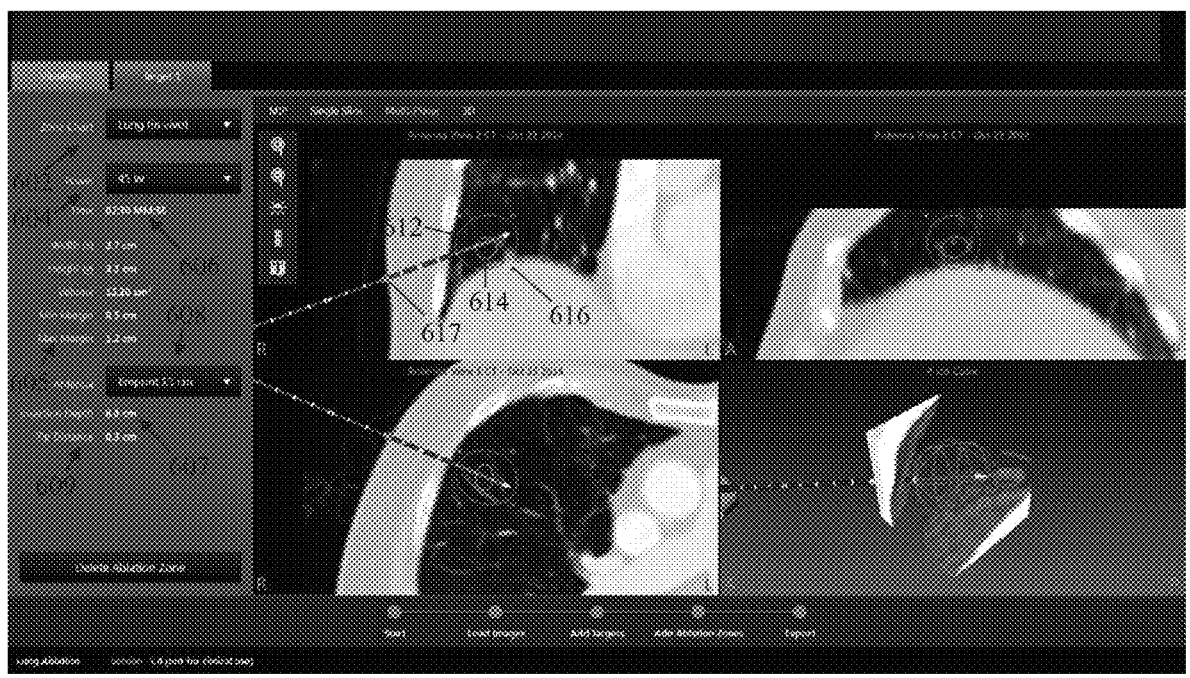

FIG. 6B illustrates changes to the user interface of FIG. 6A as a result of the user changing the settings or parameters of the surgical procedure. The user may change the settings or parameters, for example, to avoid heating nearby anatomical structures. As shown in FIG. 6B, the zone chart setting 602 is changed from "Lung (ex vivo)" to "Lung (in vivo)", the power setting is changed from 100 W to 45 W, and the antenna type setting 608 is changed from "Emprint 20 cm" to "Emprint 15 cm". Also, the position, size, and shape of the ablation zone 612 is changed as a result of the user manipulating the user-movable points 614 and 616 with a user input device such as a mouse. In particular, the user changed the position of the ablation zone 612 by moving point 614 to a different position and the user changed the size and shape of the ablation zone 612 by moving one or more of the points 616 to different positions in one or more of the views of FIGS. 6A and 6B. Further, the antenna is repositioned by selecting and moving the point 617. As shown in FIG. 6B, the point 617 is moved to indicate the outside surface of the patients' body.

Figure 7:
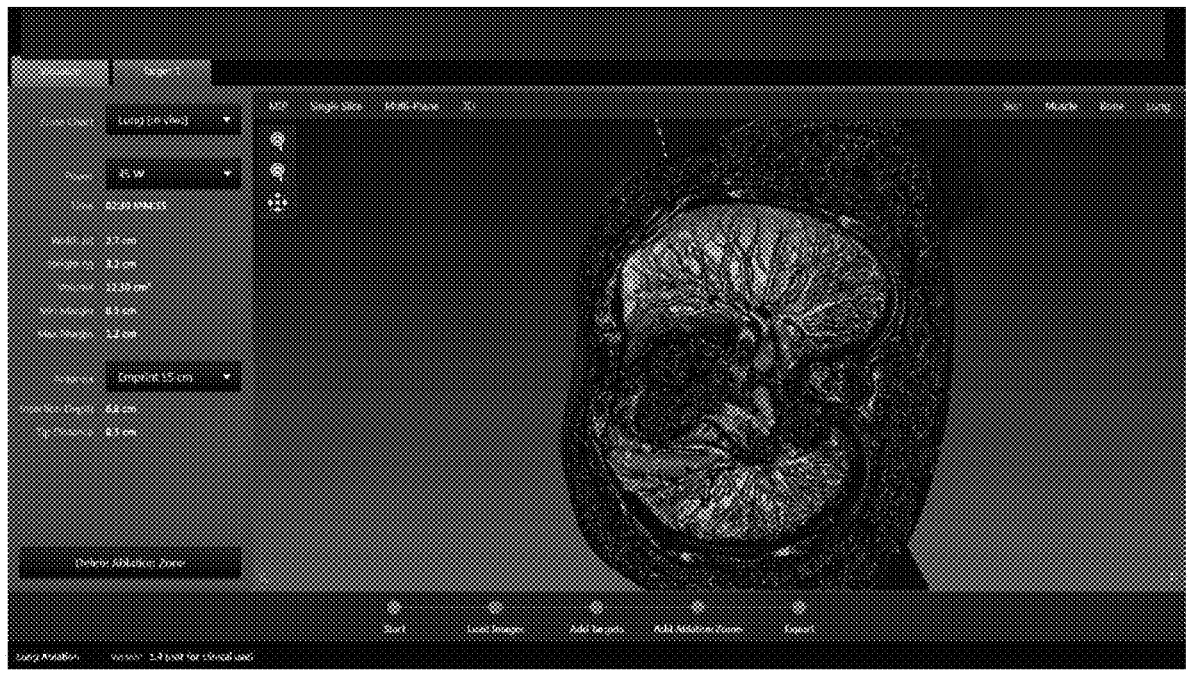
FIG. 7 is an exemplary display interface for showing different types of views of the placement and operation of an ablation instrument in accordance with aspects of this disclosure.

As a result the changes in the settings, the time information 606 changed from 8 minutes and 30 seconds to 2 minutes and 30 seconds, the width of the ablation zone changed from 3.5 cm to 2.7 cm, the height changed from 4.0 cm 3.2 cm, the volume changed from 25.75 cm$^3$ to 12.30 cm$^3$, the min margin changed from 1.0 cm to 0.5 cm, the max margin changed from 1.5 cm to 1.2 cm, the insertion depth 607 changed from "--" to 6.8 cm, and the tip distance 609 changed from 0.5 cm to 0.3 cm. In the example of FIG. 6B, the user was able to change the settings so that the ablation zone would not intersect with nearby anatomical features. In this way, the user interface of FIGS. 6A and 6B allow a user to change various settings or parameters of an ablation procedure while viewing the axial, coronal, sagittal, and 4 cm Cube views of the patient's relevant anatomy. When a user selects the "3D" icon, a cross-sectional, three-dimensional, skin view of the patient's entire body is shown in FIG. 7. This view may help the clinician to plan an ablation procedure in the context of the entire body of the patient.

FIG. 7 shows the ablation antenna inserted into the patient's lung according to the parameters set in FIG. 6B.

FIG. 7 also shows the target as a solid three-dimensional sphere and shows the ablation zone as a three-dimensional wireframe. In the three-dimensional view of FIG. 7, the user may switch the user interface from the skin view to a muscle view, a bone view, or a lung view, by selecting the corresponding icon.

In embodiments, images of the various display interfaces of FIGS. 4-7 may be captured by selecting the camera icon. The clinician may capture images of the display interfaces and save them in a patient's electronic medical records so that the clinician may later reference the images in preparation for or during an ablation procedure.

Figure 8:
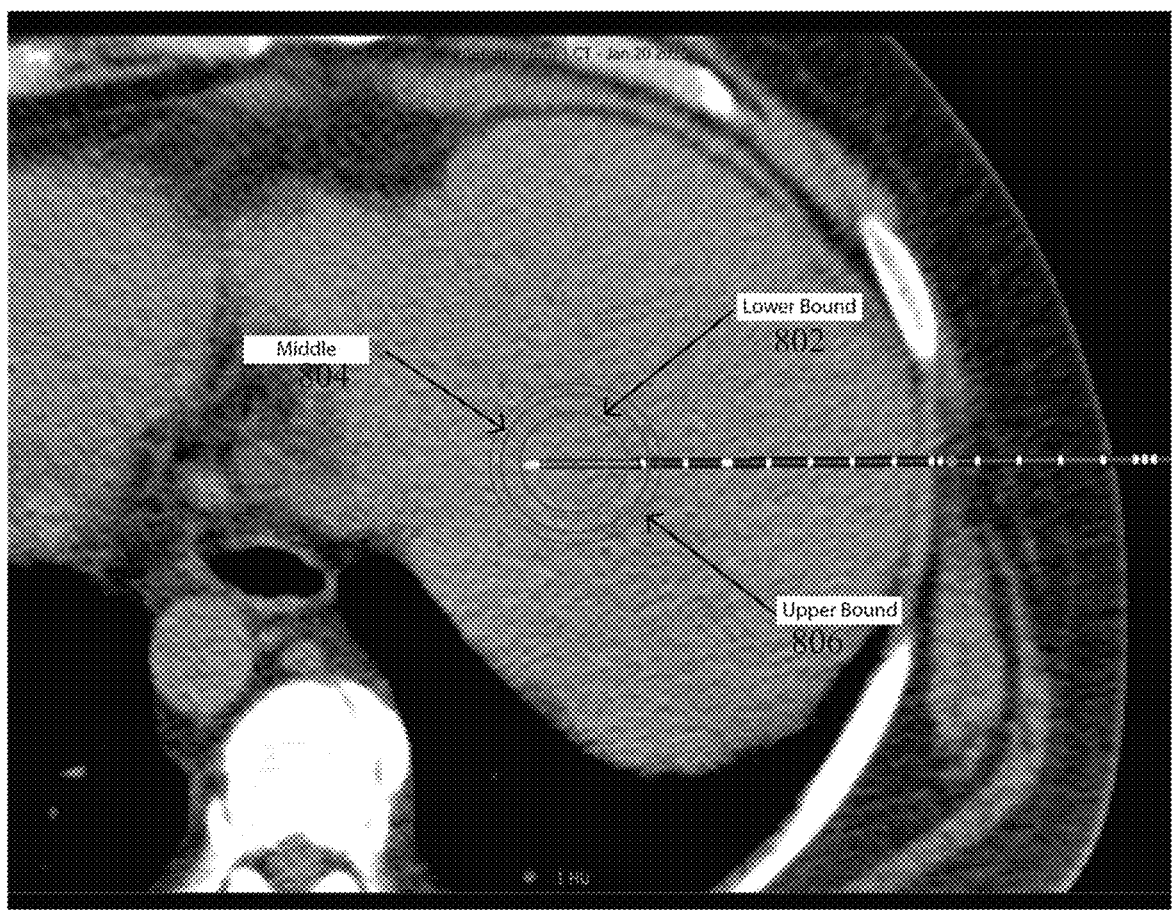
FIG. 8 is an exemplary display interface illustrating the bounds of a selectively adjustable ablation zone in an axial view in accordance with aspects of this disclosure.

FIG. 8 is an exemplary display interface illustrating the bounds of a selectively adjustable ablation zone in an axial view in accordance with aspects of this disclosure. As described above, user movable points are provided to enable a user to change the size of the ablation zone. However, the user interface places bounds on the size of the ablation zone to reflect the actual capabilities of the ablation antenna. As illustrated in FIG. 8, the ablation zone has a lower bound 802, a middle bound 804, and an upper bound 806. The ablation zone bounds may depend on, among other things, the available power level settings. For example, the upper bound 806 may relate to a 100 W power level setting, the middle bound 804 may relate to a 75 W power level setting, and the lower bound 802, may relate to a 45 W setting.

Figure 9:
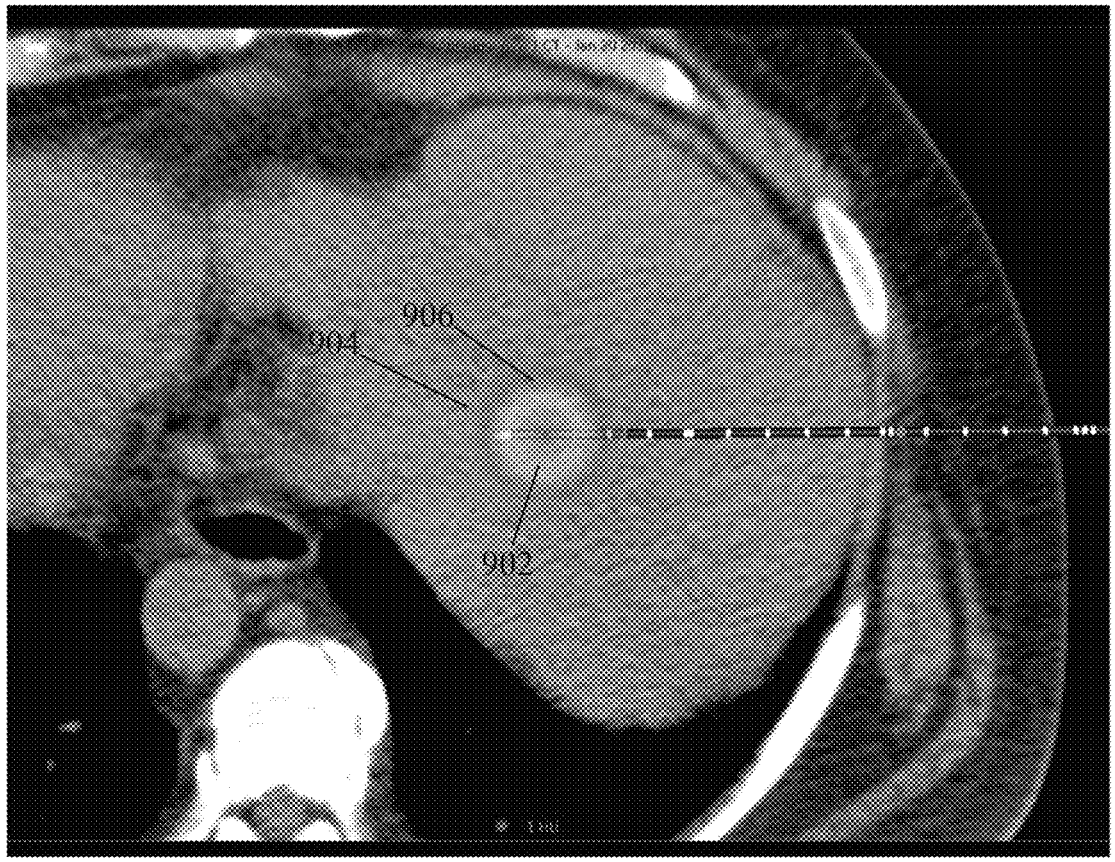
FIG. 9 is an exemplary display interface for showing a temperature profile within an ablation zone in accordance with aspects of this disclosure.

FIG. 9 is an exemplary display interface for showing a temperature profile within an ablation zone in accordance with aspects of this disclosure. The display interface may show a target with a circle 902 of a first color (e.g., green), an ablation zone with a circle 904 of a second color (e.g., red) different than the first color, and an area 906 within the circle 904 may be filled in with a range of colors (e.g., yellow, green, blue) representing a temperature profile when the ablation antenna is activated.

Figure 10:
FIG. 10 is an exemplary display interface for showing a temperature gradient surrounding an ablation zone in accordance with aspects of this disclosure.

FIG. 10 is an exemplary display interface showing a temperature profile represented by a temperature gradient 1002 in a multi-plane view of a patient's liver region in accordance with aspects of this disclosure. More specifically, FIG. 10 shows an ablation antenna inserted into a liver 1000 and a circle 1004 representing an ablation zone about a distal portion of the ablation antenna and surrounding an ablation target. The circle 1004 is surrounded by the temperature gradient 1002 to demonstrate projected temperature levels on structures and/or portions of the liver 1000 that neighbor the ablation target. In aspects of this disclosure, the temperature gradient 1002 may be animated and be represented by any one or more colors.

Figure 11:
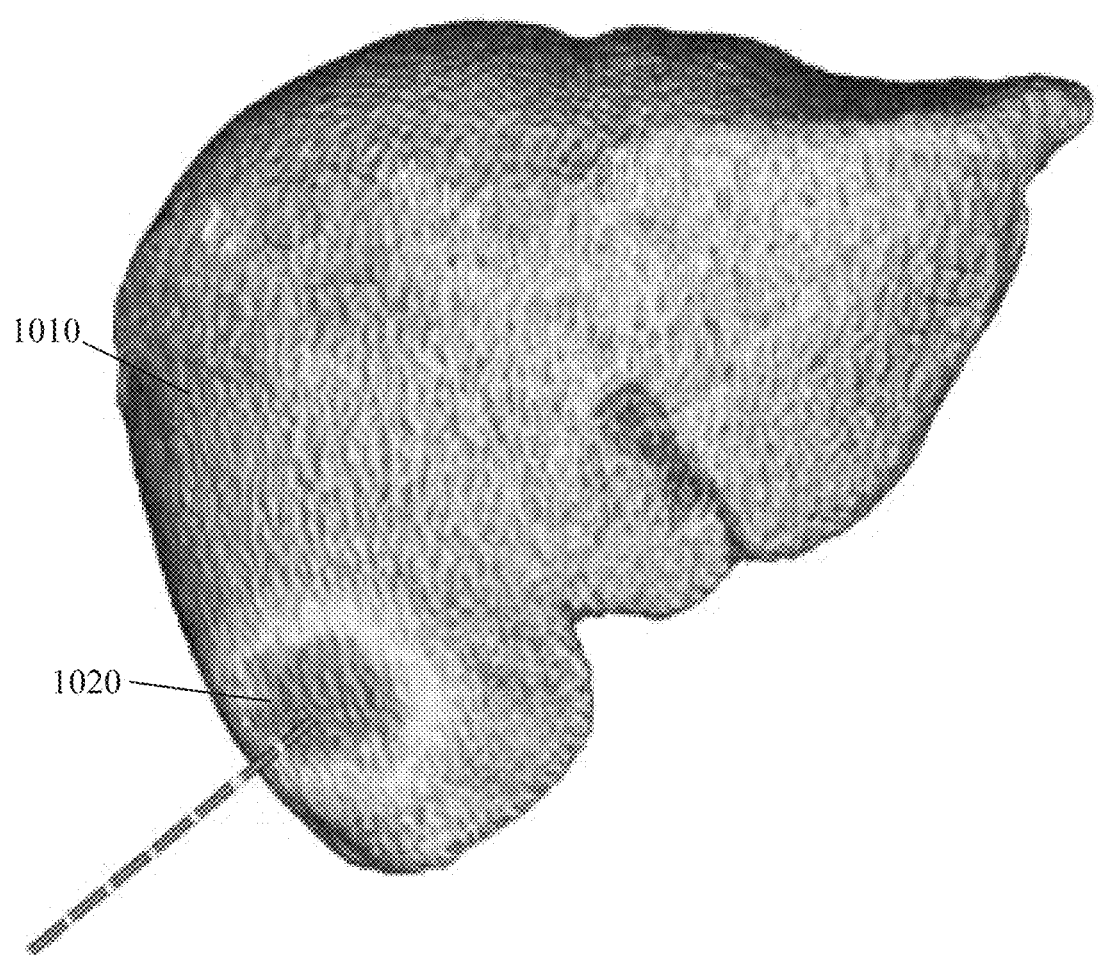
FIG. 11 is an exemplary display interface for showing a temperature profile on a three-dimensional view of a liver during a simulated or actual ablation procedure in accordance with aspects of this disclosure.

FIG. 11 is an exemplary display interface for showing a temperature profile on a three-dimensional view of a liver 1010 during a simulated or actual ablation procedure in accordance with aspects of this disclosure. A temperature profile may be represented by a range of colors 1020 (e.g., red, orange, yellow, green, blue) on the surface of the liver 1010.

Figure 12:
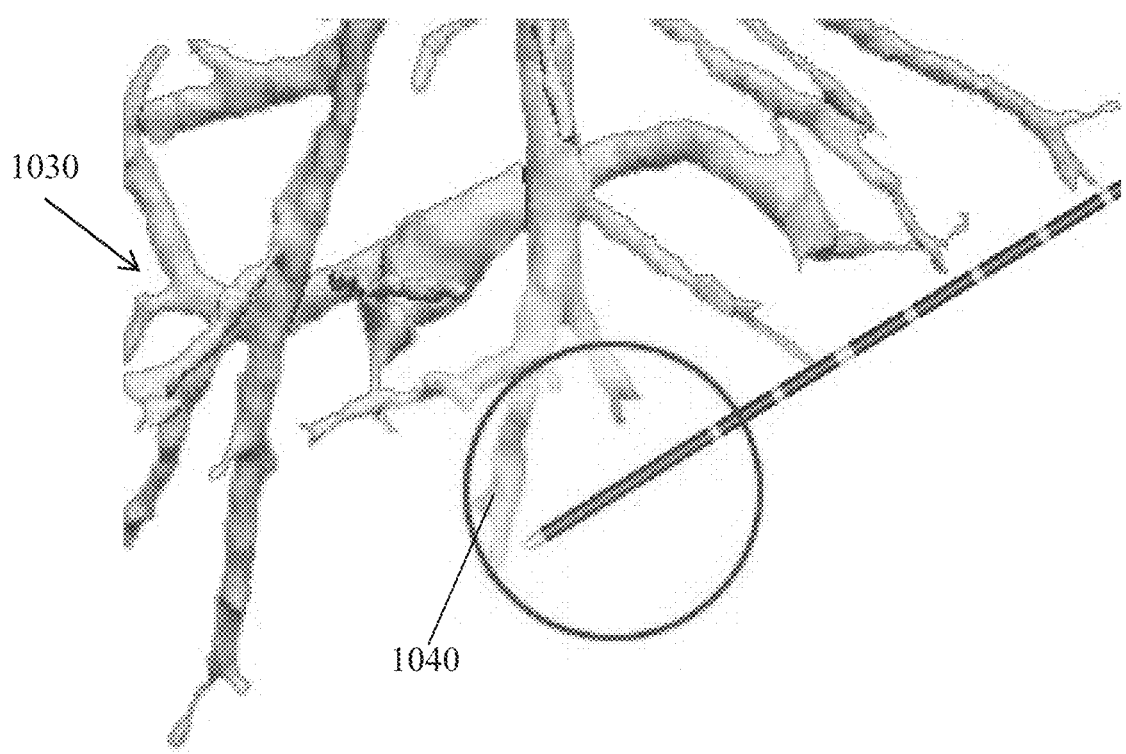
FIG. 12 is an exemplary display interface for showing a temperature profile on a three-dimensional view of a lung during a simulated or actual ablation procedure in accordance with aspects of this disclosure.

FIG. 12 is an exemplary display interface for showing a temperature profile on a three-dimensional view of a lung 1030 during a simulated or actual ablation procedure in accordance with aspects of this disclosure. A temperature profile may be represented by a range of colors 1040 on the surface of various portions of the lung 1030 to demonstrate projected temperature levels on structures and/or portions of the lung 1030 that neighbor an ablation target.

Figure 13:
FIG. 13 is an exemplary display interface illustrating the bounds of an ablation zone in multiple plane views in accordance with aspects of this disclosure.
Figure 14:
FIG. 14 is an exemplary display interface illustrating the bounds of an ablation zone in multiple plane views in accordance with aspects of this disclosure.

FIGS. 13 and 14 are exemplary display interfaces illustrating the bounds of an ablation zone in a multi-plane (e.g., axial, coronal, sagittal) view in accordance with aspects of this disclosure. The user interface places bounds on the size of the ablation zone to reflect the actual capabilities of the ablation antenna. As illustrated in FIG. 13, the ablation zone has a lower bound 1050 and an upper bound 1052. As illustrated in FIG. 14, one or more of the multi-plane (e.g., axial, coronal, sagittal) views illustrates an average bound 1060 on the size of the ablation zone, which represents an average of a lower bound 1062 and an upper bound 1064 illustrated in a detailed view of the user interface (e.g., in the upper right window of the user interface). The ablation zone bounds may depend on, among other things, the available power level settings. For example, the upper bounds 1052, 1064 may relate to a 150 W power level setting and the lower bounds 802, 1062 may relate to a 75 W setting.

Figure 15:
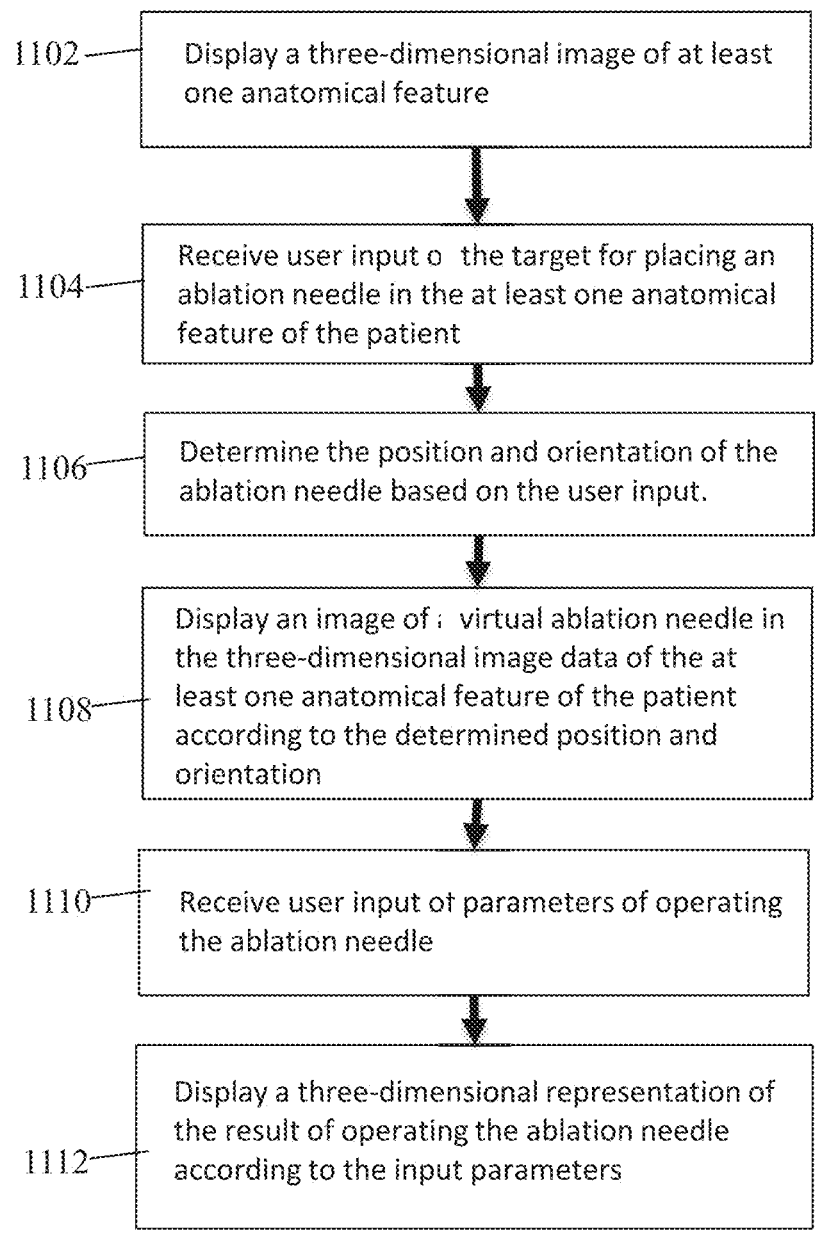
FIG. 15 is a flow diagram of an exemplary operation of a system in accordance with aspects of this disclosure.

FIG. 15 is a flow diagram of an exemplary operation of a system in accordance with aspects of this disclosure. The system may be operated as part of a planning phase or as part of an actual ablation procedure. At block 1102, a three-dimensional image of at least one anatomical feature is displayed. For example, a three-dimensional image of a liver may be displayed. At block 1104, user input of a target for placing an ablation needle in the at least one anatomical feature of the patient is received. The user input may include a user manipulating a mouse to select a location on the three-dimensional image. At block 1106, the position and orientation of the ablation needle is determined based on the user input. At block 1108, an image of a virtual ablation needle is displayed in the three-dimensional image data of the at least one anatomical feature of the patient according to the determined position and orientation. At block 1110, user input of one or more parameters of operating the ablation needle are received. The one or more parameters may include the type of ablation needle or the power level. And, at block 1112, a three-dimensional representation of the result of operating the ablation needle according to the input parameters is displayed.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto. For example, while this disclosure makes reference to some parameters relevant to an ablation procedure, this disclosure contemplates other parameters that may be helpful in planning for or carrying out an ablation procedure including a type of microwave generator, a power-level profile, or a property of the tissue being ablated.

What is claimed is:

1. A system for visualizing a projected ablation zone, comprising:
   one or more processors; and
   one or more processor-readable media storing instructions which, when executed by the one or more processors, cause performance of:
      displaying, on an image of an anatomical structure within a patient, a target for placing an ablation antenna for delivery of ablation energy to the patient at the target;
      displaying a projected ablation zone surrounding the target, the projected ablation zone corresponding to an ablation zone that would result from delivery of the ablation energy to the patient via the ablation antenna;

displaying a lower bound of the projected ablation zone surrounding the target, the lower bound corresponding to the ablation zone that would result from delivery of the ablation energy to the patient at a first power setting; and displaying an upper bound of the projected ablation zone surrounding the lower bound and the target, the upper bound corresponding to the ablation zone that would result from delivery of the ablation energy to the patient at a second power setting greater than the first power setting.

2. The system according to claim 1, wherein the one or more processor-readable media further store instructions which, when executed by the one or more processors, cause performance of simultaneously displaying the lower and upper bounds on the image of the anatomical structure.

3. The system according to claim 1, wherein the one or more processor-readable media further store instructions which, when executed by the one or more processors, cause performance of receiving input at the display of the anatomical structure to change at least one of a size or a shape of the projected ablation zone.

4. The system according to claim 1, wherein the one or more processor-readable media further store instructions which, when executed by the one or more processors, cause performance of displaying a middle bound of the projected ablation zone surrounded by the upper bound, the middle bound corresponding to the ablation zone that would result from delivery of ablation energy to the patient at a third power setting greater than the first power setting and less than the second power setting.

5. The system according to claim 4, wherein the one or more processor-readable media further store instructions which, when executed by the one or more processors, cause performance of displaying the lower, middle, and upper bounds simultaneously on the image of the anatomical structure.

6. The system according to claim 4, wherein the third power setting corresponds to delivery of the ablation energy to the patient at about 75 watts.

7. The system according to claim 1, wherein the one or more processor-readable media further store instructions which, when executed by the one or more processors, cause performance of displaying at least one movable point configured to be manipulated via input at the display of the image of the anatomical structure to change at least one of a size or a shape of the projected ablation zone.

8. The system according to claim 7, wherein the at least one movable point includes a plurality of movable points surrounding at least one of the lower or upper bounds.

9. The system according to claim 1, wherein the one or more processor-readable media further store instructions which, when executed by the one or more processors, cause performance of displaying the target in a first color and displaying the lower and upper bounds in a second color different than the first color.

10. The system according to claim 1, wherein the first power setting corresponds to delivery of the ablation energy to the patient at about 45 watts.

11. The system according to claim 1, wherein the second power setting corresponds to delivery of the ablation energy to the patient at about 100 watts.

12. One or more non-transitory processor readable media storing instructions which, when executed by one or more processors, cause performance of:

displaying a target for placing an ablation antenna for delivery of ablation energy to a patient at the target;

displaying a projected ablation zone surrounding the target, the projected ablation zone corresponding to an ablation zone that would result from delivery of the ablation energy to the patient via the ablation antenna;

displaying a first bound of the projected ablation zone surrounding the target, the first bound corresponding to the ablation zone that would result from delivery of the ablation energy to the patient at a first power setting; and displaying a second bound of the projected ablation zone surrounding the first bound and the target, the second bound corresponding to the ablation zone that would result from delivery of the ablation energy to the patient at a second power setting greater than the first power setting.

13. The one or more non-transitory processor-readable media according to claim 12, wherein the one or more non-transitory processor-readable media store further instructions which, when executed by the one or more processors, cause performance of displaying a third bound of the projected ablation zone surrounding the target and the first bound, the third bound corresponding to the ablation zone that would result from delivery of the ablation energy to the patient at a third power setting greater than the first power setting.

14. The one or more non-transitory processor-readable media according to claim 13, wherein the one or more non-transitory processor-readable media store further instructions which, when executed by the one or more processors, cause performance of simultaneously displaying the first, second, and third bounds.

15. The one or more non-transitory processor-readable media according to claim 13, wherein the third power setting corresponds to delivery of the ablation energy to the patient at about 75 watts.

16. The one or more non-transitory processor-readable media according to claim 12, wherein the one or more non-transitory processor-readable media store further instructions which, when executed by the one or more processors, cause performance of displaying at least one movable point configured to be manipulated via input at the display of the image of the anatomical structure to change at least one of a size or a shape of the projected ablation zone.

17. The one or more non-transitory processor-readable media according to claim 16, wherein the at least one movable point includes a plurality of movable points surrounding at least one of the first or second bounds.

18. The one or more non-transitory processor-readable media according to claim 12, wherein the first power setting corresponds to delivery of the ablation energy to the patient at about 45 watts.

19. The one or more non-transitory processor-readable media according to claim 12, wherein the second power setting corresponds to delivery of the ablation energy to the patient at about 100 watts.

20. A system, comprising:
one or more processors; and
one or more processor-readable media storing instructions which, when executed by the one or more processors, cause performance of:
displaying a projected ablation zone surrounding a target within a patient, the projected ablation zone corresponding to an ablation zone that would result from delivery of ablation energy to the patient;

displaying a first bound of the projected ablation zone, the first bound corresponding to the ablation zone that would result from delivery of the ablation energy to the patient at a first power setting; and displaying, simultaneously with the first bound, a second bound of the projected ablation zone surrounding the first bound, the second bound corresponding to the ablation zone that would result from delivery of the ablation energy to the patient at a second power setting greater than the first power setting.

\* \* \* \* \*